| United States Patent [19] | [11] Patent Number: 4,937,396 |
| Pews et al. | [45] Date of Patent: Jun. 26, 1990 |

[54] PREPARATION OF 3,4-DIFLUOROBENZOTRIFLUORIDE

[75] Inventors: R. Garth Pews, Midland, Mich.; Jack C. Little, Lafayette, Calif.; James A. Gall, Midland, Mich.

[73] Assignee: The Dow Chemical Company, Midland, Mich.

[21] Appl. No.: 276,711

[22] Filed: Nov. 28, 1988

[51] Int. Cl.$^5$ .................. C07C 17/20; C07C 21/24
[52] U.S. Cl. ........................... 570/144; 570/127
[58] Field of Search ....................... 570/144, 147

[56] References Cited

U.S. PATENT DOCUMENTS

| 3,408,412 | 10/1968 | Blackley et al. | 570/147 |
| 3,453,337 | 7/1969 | Bennett et al. | 570/147 |
| 4,388,472 | 6/1983 | Cartwright et al. | 560/21 |
| 4,590,315 | 5/1986 | Maul et al. | 570/127 |
| 4,684,734 | 8/1987 | Kaieda et al. | 570/147 |

FOREIGN PATENT DOCUMENTS

| 289036 | 11/1988 | European Pat. Off. |  |
| 51128 | 3/1982 | Japan . |  |
| 139329 | 8/1984 | Japan | 570/144 |
| 228436 | 11/1985 | Japan | 570/147 |

OTHER PUBLICATIONS

Yakobson et al., "Recent Synthetic Methods for Polyfluoroaromatic Compound" Synthesis, pp. 652–656 10–1976.

*Primary Examiner*—J. E. Evans
*Attorney, Agent, or Firm*—Craig E. Mixan; Ronald G. Brookens

[57] ABSTRACT

3,4-Difluorobenzotrifluoride is prepared by contacting a 3,4-dihalobenzotrifluoride with an effective amount of KF or CsF in a polar aprotic solvent at an elevated temperature under substantially anhydrous conditions. The product can be removed as it is formed or the reaction may be run at the autogenous pressures generated by the reaction mixture in a sealed reactor.

3 Claims, No Drawings

PREPARATION OF 3,4-DIFLUOROBENZOTRIFLUORIDE

FIELD OF INVENTION

The present invention relates to the preparation of ring-fluorinated benzotrifluorides from the corresponding ring-chlorinated benzotrifluorides. More particularly, the present invention is directed to the preparation of difluorobenzotrifluorides using potassium fluoride (KF) and/or cesium fluoride (CsF) as the fluorinating agent.

BACKGROUND OF THE INVENTION

Difluorobenzotrifluorides are useful intermediates for the manufacture of herbicides. For example, U.S. Pat. No. 4,642,338 discloses the use of 3,4-difluorobenzotrifluoride in the preparation of aryloxyphenoxy herbicides that control grassy weeds in the presence of broadleaf crops.

Conventional methods of preparing 3,4-difluorobenzotrifluoride are based primarily on diazotization routes involving a number of steps. In U.S. Pat. No. 4,642,338, for example, 3,4-difluorobenzotrifluoride was prepared by (a) treating 4-chloro-3-nitrobenzotrifluoride with KF, (b) reducing the nitro group to an amine, (c) diazotizing and preparing the fluoroborate salt and (d) decomposing to the desired product

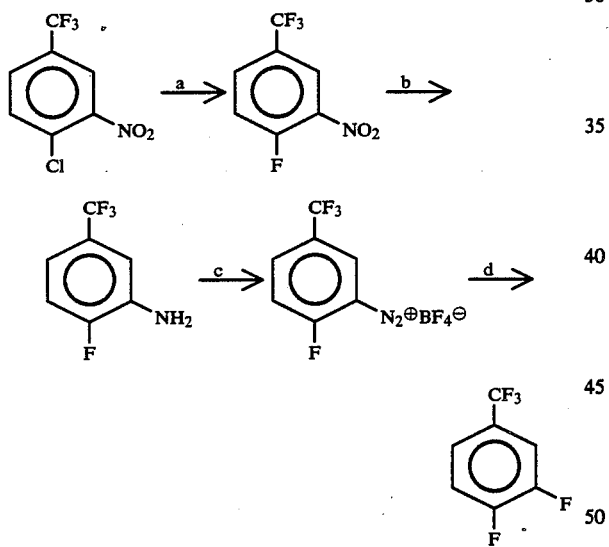

A similar scheme was employed by Schaefer et al. in *Can. J. Chem.*, 57, 802 (1979).

Alternatively, Musgrave et al. in *J. Chem. Soc. C*, 1547 (1971) describe the preparation of 3,4-difluorobenzotrifluoride by (e) the treatment of hexafluorocyclohexadiene with trifluoromethylacetylene followed by (f) pyrolysis.

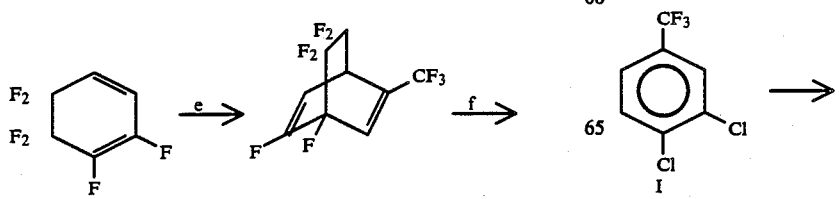

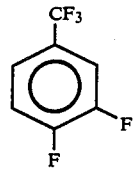

Although highly fluorinated aromatic compounds can be prepared from perhalogenated aromatic compounds or perhalogenated aromatic compounds containing one or more electron-withdrawing substituents by the action of alkali metal fluorides, it was believed that this reaction was of preparative interest only for producing completely halogenated compounds and that reactions between incompletely halogenated aromatic compounds and KF were accompanied by numerous side reactions and poor yields. (See, for example, Yakobson et al. in *Synthesis*, 652, Oct. 1976).

SUMMARY OF THE INVENTION

We have now found that, contrary to this belief, incompletely ring-fluorinated benzotrifluorides can be prepared in good yield by the action of KF or CsF on the corresponding ring-chlorinated benzotrifluorides. The present invention is directed to a method for preparing 3,4-difluorobenzotrifluoride which comprises contacting a 3,4-dihalobenzotrifluoride of the formula

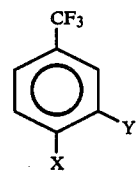

wherein X and Y are independently F or Cl provided at least one of X and Y is Cl, with an effective amount of KF or CsF under substantially anhydrous conditions in a suitable polar aprotic solvent at a temperature so that fluorine exchange readily occurs, and recovering the 3,4-difluorobenzotrifluoride from the reaction mixture.

Surprisingly, the present invention allows for the preparation of incompletely fluorinated benzotrifluorides from the corresponding chlorinated benzotrifluorides in good yield with a minimum of side reactions. The conversion may be effectively accomplished with both CsF and the mush less expensive KF.

DETAILED DESCRIPTION OF THE INVENTION

The conversion of 3,4-dichlorobenzotrifluoride (I) to 3,4-difluorobenzotrifluoride (II) is a stepwise process which involves the intermediacy of a singularly fluorine-exchanged compound (III), either 3-fluoro-4-chlorobenzotrifluoride and/or 3-chloro-4-fluorobenzotrifluoride.

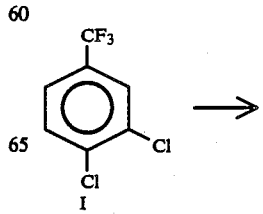

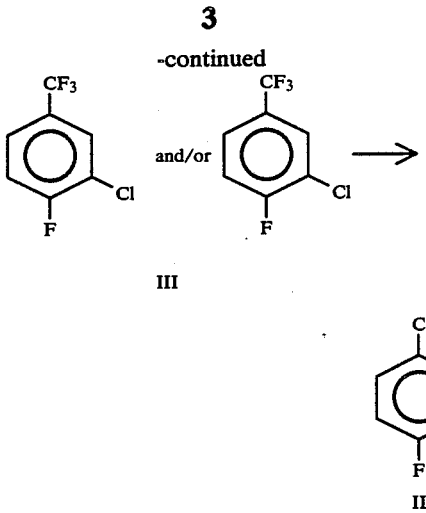

Optionally, the reaction can be conducted in a fashion so that the singularly fluorine-exchanged fluorochlorobenzotrifluoride (FCBTF) is obtained as the major product.

KF and CsF are the fluorinating agents employed in the present reaction and are commercially available compounds. Substantially anhydrous and finely-divided KF or CsF are preferred. Amorphous or spray-dried forms are particularly preferred. Substantially anhydrous KF and CsF can be prepared, for example, by drying in vacuo at 140°–250° C. for several hours.

3,4-dichlorobenzotrifluoride is also a commercially available compound.

Polar aprotic diluents are employed as the reaction medium in the present process. Suitable polar aprotic diluents include dimethyl sulfoxide (DMSO), dimethyl formamide (DMF), dimethyl acetamide (DMA), hexamethyl phosphoric acid triamide (HMPA), sulfolane, N-methyl pyrrolidinone (NMP), N-cyclohexyl pyrrolidinone (NCHP), 1,3-dimethyl-2-imidazolidinone (DMI) and 1,3-dimethyl-3,4,5,6-tetrahydro-2-(1H)pyrimidone (DMTHP), and benzonitrile. Preferred diluents include NMP, DMI, DMTHP, DMSO and sulfolane.

Optionally, the reaction may be conducted in the presence of (a) an acid scavenger, such as, an alkali metal carbonate, and/or in the case of employing KF as the fluorinating agent, (b) a phase-transfer catalyst.

The present reaction is conducted under substantially anhydrous conditions at elevated temperatures of from about 140° to about 300° C. Preferred temperature ranges are from about 175° to about 275° C. when CsF is used, and from about 240° to about 295° C. when KF is used.

Pressures of from atmospheric to greater than atmospheric are typically employed. For CsF, which is more reactive than KF, it is most convenient to operate at atmospheric pressure. For KF, which is less expensive than but also less reactive than CsF, it is preferred to operate at the autogenous pressure generated by the diluent, starting material and product in a sealed reactor at the preferred reaction temperatures of 240° to 295° C. Such pressures typically range from slightly above atmospheric to about 500 pounds per square inch (psi) and depend upon the volume of the reactor. Optionally, the reaction can be run under pressure in a suitably designed reactor equipped with a distillation column so the product can be removed as formed.

Water is detrimental to the reaction and substantially anhydrous reaction conditions are preferred. By substantially anhydrous is meant that the reaction medium contains less than about 500 parts per million (ppm) water. Preferably the reaction medium contains less than about 150 ppm water. Substantially anhydrous conditions may be achieved employing standard drying techniques. For example, a typical laboratory reactor can be dried by distilling the polar aprotic solvent under a vacuum before addition of the reactants. Optionally, a small amount (5–10 percent by weight of the polar aprotic solvent) of a non-polar solvent such as an aromatic hydrocarbon (toluene, xylene, etc.) may be added to the polar aprotic solvent to aid in the removal of water by azeotropic distillation. Residual water in the reactor system is also often removed by azeotropic distillation.

The amount of polar aprotic solvent is not critical, but it is advantageous to employ enough solvent to keep the starting material in solution at reaction temperatures, generally from about 2 to about 25 parts by weight of the solvent per part by weight of the benzotrifluoride starting material. The relative proportions of reactants to be employed are not critical because some of the product will be formed when employing any proportion of reactants. The reaction consumes the reactants, however, in the ratio of one mole of fluorinating agent per mole of exchangeable chlorine atoms present in the starting material. For example, with 3,4-dichlorobenzotrifluoride as the starting material, about 2 molar equivalents of KF or CsF per mole of starting material are consumed. Usually from about 1.0 to about 3.0 moles of KF or CsF are employed per mole of exchangeable chlorine in the benzotrifluoride starting material.

The present reaction is typically conducted in the presence of agitation sufficient to maintain an essentially uniform dispersion of the reactants in the solvent.

Catalysts are optionally employed to increase the reaction rate. Suitable catalysts include phase-transfer catalysts. The catalyst is added to the present reaction mixture in an amount of from about 0.0001 to about 0.1 mole per mole of benzotrifluoride starting material, advantageously from about 0.001 to about 0.075 molar equivalents and preferably from about 0.01 to about 0.05 molar equivalents.

Phase-transfer catalysts are well-known compounds and include (a) quaternary phosphonium salts containing 10 or more carbon atoms and (b) macrocyclic polyethers commonly known as crown ethers. Suitable crown ether catalysts include 18-crown-6; dicyclohexano-18-crown-6; dibenzo-18-crown-6; 15-crown-5. A related species, tris(3,6-dioxa-heptyl)amine is also efficacious. Suitable quaternary phosphonium salts include the tetra-n-alkylphosphonium salts. The anion of the phosphonium slats is $F^{\ominus}$, which may be derived from any anion which readily converts to $F^{\ominus}$, such as, for example, $Cl^{\ominus}$, $Br^{\ominus}$, $I^{\ominus}$, $OH^{\ominus}$, $OAc^{\ominus}$, etc., under the reaction conditions.

Acid scavengers are optionally employed in the present reaction to consume or inactivate traces of HCl or HF which may be present or generated during the reaction. Suitable acid scavengers include alkali metal carbonates such as anhydrous $K_2CO_3$ and anhydrous $Na_2CO_3$. A preferred acid scavenger is anhydrous $K_2CO_3$. The acid scavengers are added to the present reaction mixture in an amount of from about 0.001 to about 0.1 mole per mole of benzotrifluoride starting material. Preferably, from about 0.03 to about 0.05 molar equivalents are employed.

The 3,4-difluorobenzotrifluoride can be recovered from the reaction mixture by conventional techniques such as extraction and/or distillation. Preferably, the product is removed from the reaction mixture as it is formed. Optionally, the reactant compound may be added as the product is removed.

The product may be separated from starting material and/or intermediate fluorochlorobenzotrifluorides (FCBTF) by fractional distillation.

In carrying out the present reaction, neither the rate nor the order of addition of the reactants is critical. Usually, the solvent and fluorinating agent are added to an appropriate reaction vessel and the reaction is dried by distilling a small portion of the solvent. The starting material or precursor compound is then added to the reaction vessel. The reaction mixture is then heated to a temperature high enough to maintain a satisfactory reaction rate. The product may be recovered from the reaction mixture after completion of the reaction by extraction and or distillation. Alternatively, the product may be removed from the reaction mixture by fractional distillation as it is formed. If an acid scavenger, a nonpolar solvent, or catalyst is employed in the reaction, then they are advantageously added to the solvent/-fluorinating agent mixture prior to drying the reactor vessel.

The following examples illustrate the practice of the present invention and should not be construed as limiting.

EXAMPLE 1

To a 1 liter (L), 3-necked flask equipped with a stirrer, heat source, thermometer and temperature controller, and a 7-tray, 1" I.D. sieve plate (Oldershaw) fractionating column, was charged 600 milliliters (mL) of dimethylsulfoxide (DMSO), 159.9 gram (g) (1.05 mole) of dried CsF and 3 g of $K_2CO_3$ (acid scavenger). Approximately 40 mL of solvent was distilled in vacuo (150 mm Hg) to dry the system, and then 107.5 g (0.5 mole) of 3,4-dichlorobenzotrifluoride (Hooker Chemical Co.) was added. The mixture was heated to 177° C. at atmospheric pressure, at which point refluxing was observed in the distillation column. Heating was continued until the head temperature dropped to approximately 100° C. (2 hours) and then takeoff was commenced at such a rate as to hold the head temperature under 120° C. After a total of 5.5 hours (hr), a total of 20.8 g of distillate had been collected. Analysis (glpc) showed the presence of 15.7 g of 3,4-difluorobenzotrifluoride and 4.0 g of 3-chloro-4-fluorobenzotrifluoride. Further heating of the reaction mixture for a total of 19 hr gave an additional 29 g of distillate. Analysis of all fractions showed that a total of 21.7 g of the 3,4-difluorobenzotrifluoride was produced.

Redistillation of the volatile fractions gave purified 3,4-difluorobenzotrifluoride, b.p. 102° C., as well as the intermediate, 3-chloro-4-fluorobenzotrifluoride, b.p. 140° C.

EXAMPLE 2

To the apparatus described in Example 1 was charged 600 mL of DMSO. After distillation (at 1 atm.) of approximately 30 mL of DMSO to dry the system, 228 g (1.5 moles) of dry CsF, 107.5 g (0.5 mole) of dry 3,4-dichlorobenzotrifluoride and 3 g of $K_2CO_3$ were added. The mixture was heated with stirring to 180° C. at atmospheric pressure and total reflux on the distillation head. When the head temperature had dropped to 110° C. (2 hr), takeoff was initiated. The distillation was continued, adjusting the takeoff rate so as to keep the head temperature below 120° C. until the rate of production of 3,4-difluorobenzotrifluoride dropped off markedly (13 hr). Analysis of the distillate showed that 44.8 g of 3,4-difluorobenzotrifluoride and 5.4 g of approximately 85:15 ratio of 3-chloro-4-fluoro- and 4-chloro-3-fluorobenzotrifluoride had been recovered.

EXAMPLE 3

To the apparatus described in Example 1 was charged 600 mL of DMSO, and the system was dried by distilling 30 mL of the material at atmospheric pressure. There was then added 108 g (0.71 mole) of dry CsF, 99.3 g (0.5 mole) of a dry mixture of approximately 85% 3-chloro-4-fluoro- and 15% 4-chloro-3-fluorobenzotrifluorides, and 3 g $K_2CO_3$. The mixture was heated with stirring to 177°-186° C. at 1 atmosphere while a distillate (28.4 g), approximately consisting of 63% 3,4-difluorobenzotrifluoride and 35% starting chlorofluoro derivative, was collected at 106°-120° C. head temperature over 4.3 hr. Vacuum was then applied to the system and an additional 36.6 g of volatile material was collected. Analysis of the combined distillation cuts showed that 19.6 g of 3,4-difluorobenzotrifluoride and 42.1 g of the starting chlorofluorobenzotrifluorides had been recovered.

EXAMPLE 4

To the apparatus described in Example 1 was charged 600 mL of sulfolane and approximately 40 mL of the solvent was removed at approximately 100 mm Hg pressure to dry the system. There was then added 61 g (1.05 mole) of dry KF, 107.5 g (0.5 mole) dry, 3,4-dichlorobenzotrifluoride, 3 g of $K_2CO_3$ and 5 g (0.019 mole) of 18-crown-6 ether. The mixture was heated to 203°-210° C. at 1 atm. with a very slow takeoff rate over 24 hr, and then the pressure was reduced to 100 mm and distillation of the remaining benzotrifluoride derivatives was completed. Analysis showed that 2.2 g of 3,4-difluorobenzotrifluoride, 53.6 g of approximately 85:15 mixture of 3-chloro-4-fluoro- and 4-chloro-3-fluorobenzotrifluorides, plus 16.5 g of the starting material, 3,4-dichlorobenzotrifluoride, had been recovered.

EXAMPLE 5

To the apparatus described in Example 1 was charged 600 mL of NMP, 159.9 g (1.05 mole) of CsF and 3 g of $K_2CO_3$. Approximately 20 mL of solvent was distilled at atmospheric pressure to dry the system. There was then charged 99 g (01.5 mole) of an 85:15 mixture of 3-chloro-4-fluoro- and 4-chloro-3-fluorobenzotrifluorides, and the mixture was heated to 192° C. at atmospheric pressure and total reflux. When the head temperature dropped to 110° C. (1 hr), distillation was commenced at a rate such as to maintain the head temperature below 125° C. After 19 hr, the reaction appeared to have slowed appreciably, so the remaining volatiles were stripped. Analysis of the combined distillation cuts showed the presence of 39.1 g of 3,4-difluorobenzotrifluoride and 31 g recovered starting chlorofluorobenzotrifluorides.

EXAMPLE 6

A series of experiments were conducted under pressure in either a 300 mL or 600 mL Hastelloy "C" pressure reactor. The fluorinating agents were dried in a vacuum oven at 150° C. for at least 24 hr. Solvents were dried by distillation from calcium hydride. The starting material, fluorinating agent and diluent were introduced into the pressure reactor with a known amount of 1,3-diethylbenzene which served as an internal standard. The reactor was sealed and pressure tested. After the indicated times and temperatures, the reactor was cooled and vented and the reaction mixture was analyzed by gas chromatography. The experimental conditions and the results of these experiments are summarized in Table I.

TABLE I

Fluorine-Exchange on 3,4-Dichlorobenzotrifluoride

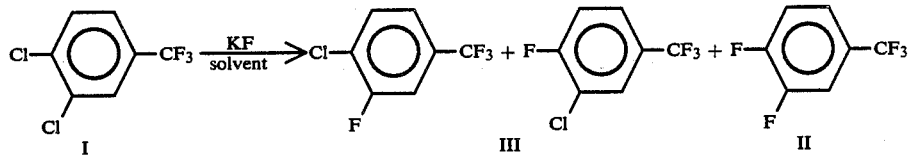

| Exp. No. | Temp °C. | Time hr | KF (Mol) | I (Mol) | KF/I | II (Mol) | III (Mol) | II/III | Mat. Bal. | Solvent | Mol I Left | mL Solvent |
|---|---|---|---|---|---|---|---|---|---|---|---|---|
| 1 | 275 | 24.25 | 0.4 | 0.2 | 2 | 0.074 | 0.096 | 0.77 | 85% | NMP | 0 | 250 |
| 2 | 275 | 24.25 | 0.8 | 0.2 | 4 | 0.092 | 0.059 | 1.55 | 76% | NMP | 0 | 250 |
| 3 | 275 | 24.33 | 0.8 | 0.2 | 4 | 0.098 | 0.068 | 1.44 | 83% | NMP | 0 | 250 |
| 4 | 275 | 24 | 0.8 | 0.2 | 4 | 0.09 | 0.06 | 1.50 | 75% | NMP | 0 | 250 |
| 5 | 275 | 8 | 0.8 | 0.2 | 4 | 0.055 | 0.132 | 0.41 | 99% | NMP | 0.011 | 250 |
| 6 | 275 | 24 | 0.8 | 0.2 | 4 | 0.081 | 0.062 | 1.30 | 71.5% | NMP | 0 | 250 |
| 7 | 275 | 24 | 0.6 | 0.2 | 3 | 0.088 | 0.065 | 1.35 | 76.5% | NMP | 0 | 250 |
| 8 | 275 | 24 | 0.6 | 0.2 | 3 | 0.088 | 0.055 | 1.60 | 71.5% | NMP | 0 | 250 |
| 9 | 275 | 24 | 0.4 | 0.2 | 2 | 0.097 | 0.05 | 1.73 | 76.5% | NMP | 0 | 250 |
| 10 | 275 | 24 | 0.8 | 0.2 | 4 | 0.052 | 0.133 | 0.46 | 82.5% | NMP | 0 | 250 |
| 11 | 275 | 24 | 0.8 | 0.2 | 4 | 0 | 0.35 | — | 116% | Benzo-nitrile | 0.196 | 250 |
| 12 | 275 | 24 | 0.8 | 0.2 | 4 | 0.067 | 0.079 | 0.84 | 73% | Sul-folane | 0 | 250 |
| 13 | 275 | 24 | 0.2 | 0.1 MFBTF | 2 | 0.033 | 0.046 | 0.71 | 79% | NMP | 0 | 125 |
| 14 | 275 | 24 | 0.2 | 0.1 MFBTF | 2 | 0.019 | 0.039 | 0.48 | 58% | NMP | 0 | 125 |
| 15 | 285 | 24 | 0.8 | 0.2 | 4 | 0.087 | 0.061 | 1.42 | 74% | NMP | 0 | 250 |
| 16 | 265 | 24 | 0.8 | 0.2 | 4 | 0.074 | 0.098 | 0.75 | 86% | NMP | 0 | 250 |
| 17 | 260 | 24 | 0.8 | 0.2 | 4 | 0.054 | 0.12 | 0.45 | 87% | NMP | 0 | 250 |
| 18 | 225 | 24 | 0.8 | 0.2 | 4 | 0.013 | 0.157 | 0.08 | 94.5% | NMP | 0.019 | 250 |
| 19 | 250 | 24 | 0.8 | 0.4 | 4 | 0.047 | 0.156 | 0.30 | 101.5% | NMP | 0 | 250 |
| 20 | 275 | 24 | 0.8 | 0.2 | 4 | 0.083 | 0.031 | 2.67 | 57% | DMTHP | 0 | 250 |
| 21 | 275 | 24 | 0.8 | 0.2 | 4 | 0.011 | 0.109 | 0.10 | 70% | NCHP | 0.02 | 250 |
| 22 | 260 | 24 | 0.8 | 0.2 | 4 | 0.053 | 0.083 | 0.63 | 68% | DMTHP | 0 | 250 |
| 23 | 240 | 24 | 0.8 | 0.2 | 4 | 0.026 | 0.109 | 0.23 | 70.7% | DMTHP | 0 | 250 |
| 24 | 250 | 24 | 0.4 | 0.1 | 4 | 0.02 | 0.056 | 0.35* | 76% | DMTHP | 0 | 125 |
| 25 | 260 | 24 | 0.4 | 0.1 | 4 | 0.026 | 0.057 | 0.45 | 85% | DMI | 0.002 | 125 |
| 26 | 275 | 12 | 0.4 | 0.01 | 4 | 0 | 0.026 | — | 103% | NMP | 0.077 | 125 |
| 27 | 275 | 12 | 0.4 | 0.1 | 4 | 0.042 | 0.041 | 1.02 | 83% | DMI | 0 | 125 |
| 28 | 275 | 12 | 0.4 | 0.1 | 4 | 0.05 | 0.037 | 1.35 | 87% | DMI | 0 | 125 |
| 29 | 260 | 12 | 0.4 | 0.1 | 4 | 0.027 | 0.06 | 0.45 | 87% | DMI | 0 | 125 |
| 30 | 260 | 12 | 0.4 | 0.1 | 4 | 0.028 | 0.061 | 0.45 | 89% | DMI | 0 | 125 |
| 31 | 260 | 24 | 0.4 | 0.1 | 4 | 0.04 | 0.044 | 0.90 | 88% | DMI | 0 | 125 |
| 32 | 260 | 24 | 0.4 | 0.1 | 4 | 0.047 | 0.042 | 1.11 | 89% | DMI | 0 | 125 |
| 33 | 275 | 24 | 0.4 | 0.1 | 4 | 0.057 | 0.023 | 2.47 | 80% | DMI | 0 | 125 |
| 34 | 275 | 24 | 0.4 | 0.1 | 4 | 0.067 | 0.017 | 3.94 | 84% | DMI | 0 | 125 |
| 35 | 275 | 12 | 0.2CsF | 0.05 | 4 | 0.035 | 0 | — | 70% | DMI | 0 | 65 |
| 36 | 260 | 12 | 0.2CsF | 0.05 | 4 | 0.047 | 0 | — | 94% | DMI | 0 | 65 |
| 37 | 275 | 12 | 0.4 | 0.1 | 4 | 0.034 | 0.048 | 0.70 | 82% | NMP | 0 | 125 |
| 38 | 275 | 12 | 0.4 | 0.1 | 4 | 0.036 | 0.051 | 0.50 | 87% | NMP | 0 | 125 |
| 39 | 275 | 12 | 0.2CsF | 0.05 | 4 | 0.02 | 0 | — | 40% | NMP | 0 | 65 |
| 40 | 275 | 12 | 0.4 | 0.1 | 4 | 0.021 | 0.066 | 0.31 | 87% | NMP | 0 | 125 |
| 41 | 275 | 12 | 0.4 | 0.1 | 4 | 0.047 | 0.04 | 1.17 | 87% | DMI | 0 | 125 |

What is claimed is:

1. A process for preparing 3,4-difluorobenzotrifluoride which comprises contacting a 3,4-dihalobenzotrifluoride of the formula

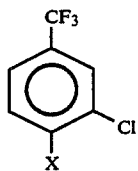

wherein X is F or Cl, with from about 1.0 to about 3.0 molar equivalents of KF per exchangeable Cl atom under substantially anhydrous conditions in a polar aprotic solvent selected from the group consisting of N-methyl pyrrolidinone, 1,3-dimethyl-2-imidazolidinone and 1,3-dimethyl-3,4,5,6-tetrahydro-2-(1H)pyrimidone at a temperature from about 240° to about 295° C. at an elevated pressure, and recovering the 3,4-difluorobenzotrifluoride from the reaction medium.

2. The process of claim 1 in which the elevated pressure is from slightly above atmospheric to about 500 pounds per square inch.

3. The process of claim 1 in which the elevated pressure is the autogenous pressure generated by the reaction mixture in a sealed reactor.

* * * * *